United States Patent [19]

Kiewit

[11] 4,107,626

[45] Aug. 15, 1978

[54] DIGITAL OUTPUT FORCE SENSOR USING SURFACE ACOUSTIC WAVES

[75] Inventor: David A. Kiewit, Arlington Heights, Ill.

[73] Assignee: Gould Inc., Rolling Meadows, Ill.

[21] Appl. No.: 752,291

[22] Filed: Dec. 20, 1976

[51] Int. Cl.² .................. G01L 1/16; H03B 5/32; H03B 21/00

[52] U.S. Cl. .................. 331/65; 73/88.5 R; 73/DIG. 4; 331/40; 331/107 A; 333/72

[58] Field of Search ............ 331/37, 40, 65, 107 A; 73/88 R, 88.5 R, 88.5 SD, DIG. 4; 333/30 R, 72

[56] References Cited

U.S. PATENT DOCUMENTS

| | | | |
|---|---|---|---|
| 3,341,796 | 9/1967 | Eisele | 338/5 |
| 3,786,373 | 1/1974 | Schulz et al. | 333/30 R |
| 3,868,608 | 2/1975 | Williams | 333/30 R X |
| 3,878,477 | 4/1975 | Dias et al. | 331/107 A X |
| 3,916,348 | 10/1975 | Toda et al. | 333/30 R |

*Primary Examiner*—Siegfried H. Grimm
*Attorney, Agent, or Firm*—Phillip H. Mayer; Eber J. Hyde; Charles E. Snee, III

[57] ABSTRACT

A sensor developing a digital output in response to force induced deflection in which the deflection is of a beam formed to have, under stress, a surface undulate in both compression and tension. The signal is developed from piezoelectric transducers connected in a pair of oscillator circuits utilizing surface acoustic wave paths through, respectively, the tension and the compression portions of the beam surface. The frequencies of the oscillators are compared and the frequency difference resulting from beam deflection is sent as a signal to a counter to give a digital read out of the force causing the deflection. The beam is formed of steel and the piezoelectric surface for the surface waves and the interdigitated conductors forming the transducers are deposited by thin film techniques on the beam.

7 Claims, 6 Drawing Figures

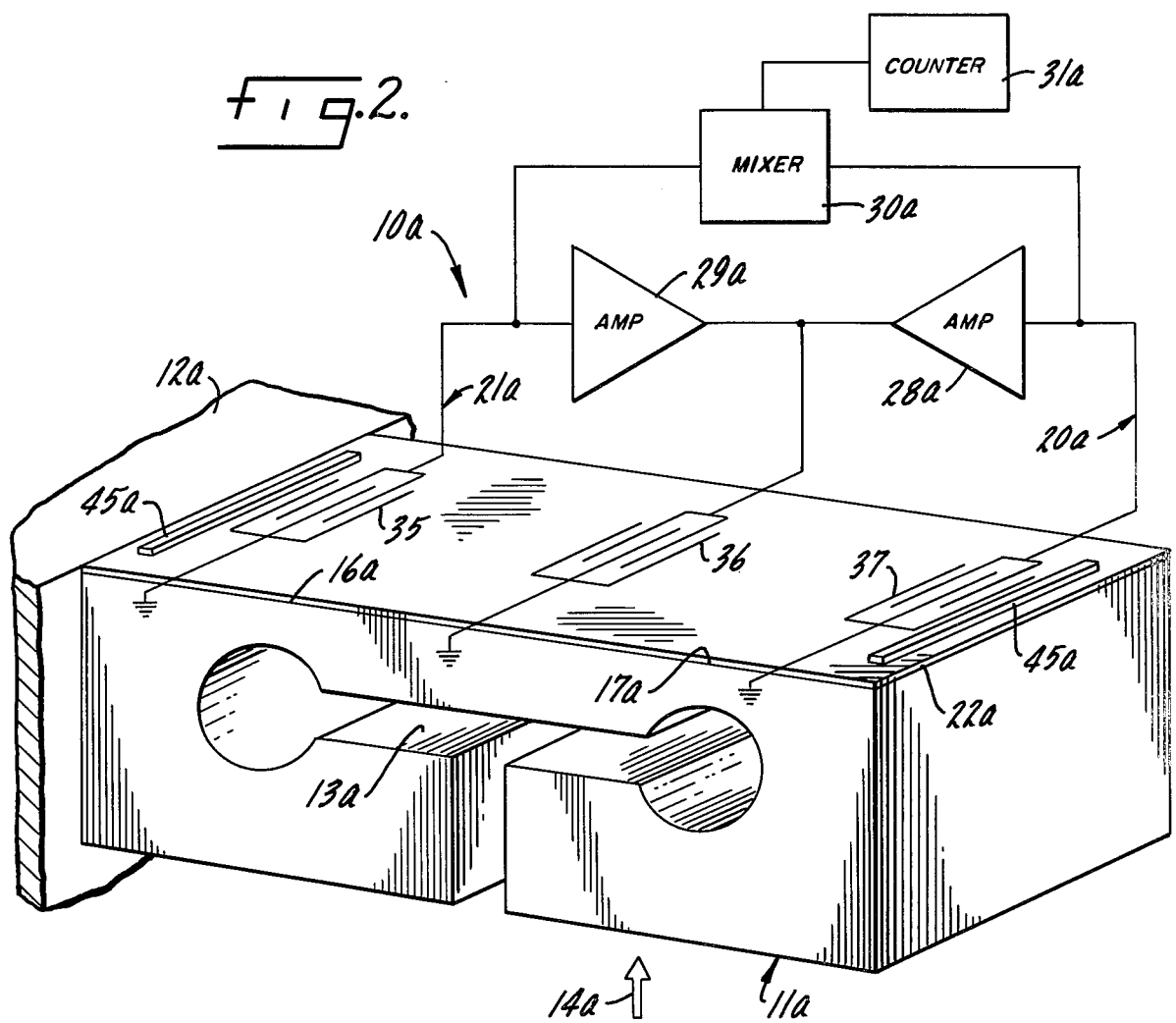
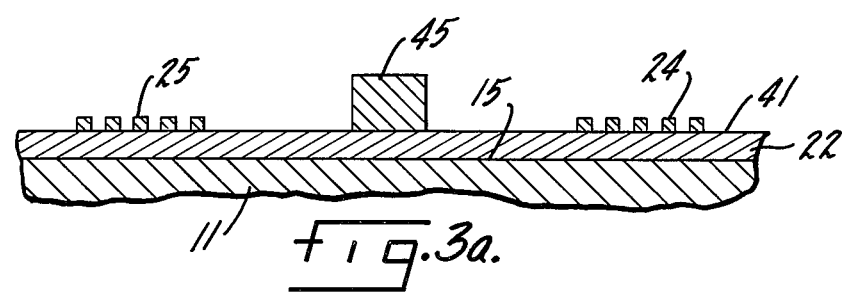
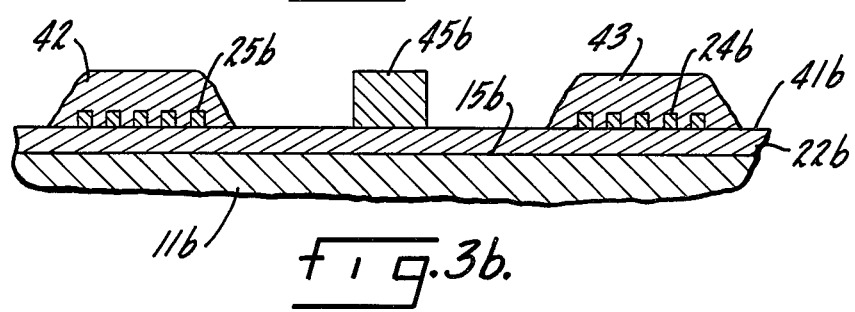

DIGITAL OUTPUT FORCE SENSOR USING SURFACE ACOUSTIC WAVES

This invention relates generally to sensors for converting mechanical strain to an electronic digital signal and more particularly concerns a sensor utilizing surface acoustic wave oscillators.

Surface acoustic wave (SAW) devices have been utilized as delay line or filter circuit components and, more recently, devices utilizing surface acoustic waves have been suggested as force sensors — see U.S. Pat. No. 3,878,477 for a disclosure of this general type. As is often the case when a relatively new technology is adapted to practical use, the resulting sensor hardware utilizing SAW principles has been complicated in design and materials so as to be expensive to manufacture and subject to mechanical breakage and resulting failure.

Accordingly, it is the primary aim of the invention to provide a SAW sensor that is accurate, temperature compensating and yet economical to manufacture.

A related object of the invention is to provide a sensor of this type which is rugged and quite resistant to shock and mechanical vibration.

Another object is to provide a sensor as characterized above that is well suited for delivering a digital output.

Other objects and advantages of the invention will become apparent upon reading the following detailed description and upon reference to the drawings, in which:

FIG. 2 is similar to FIG. 1 but showing a modification of that sensor;

FIG. 3a is an enlarged partial cross section taken along line 3—3 of a portion of the surface of the sensor of FIG. 1;

FIG. 3b is similar to FIG. 3a but showing a modification of that surface portion.

While the invention will be described in connection with a preferred embodiment, it will be understood that I do not intent to limit the invention to that embodiment. On the contrary, I intend to cover all alternatives, modifications and equivalents as may be included within the spirit and scope of the invention as defined by the appended claims.

Figure 1:
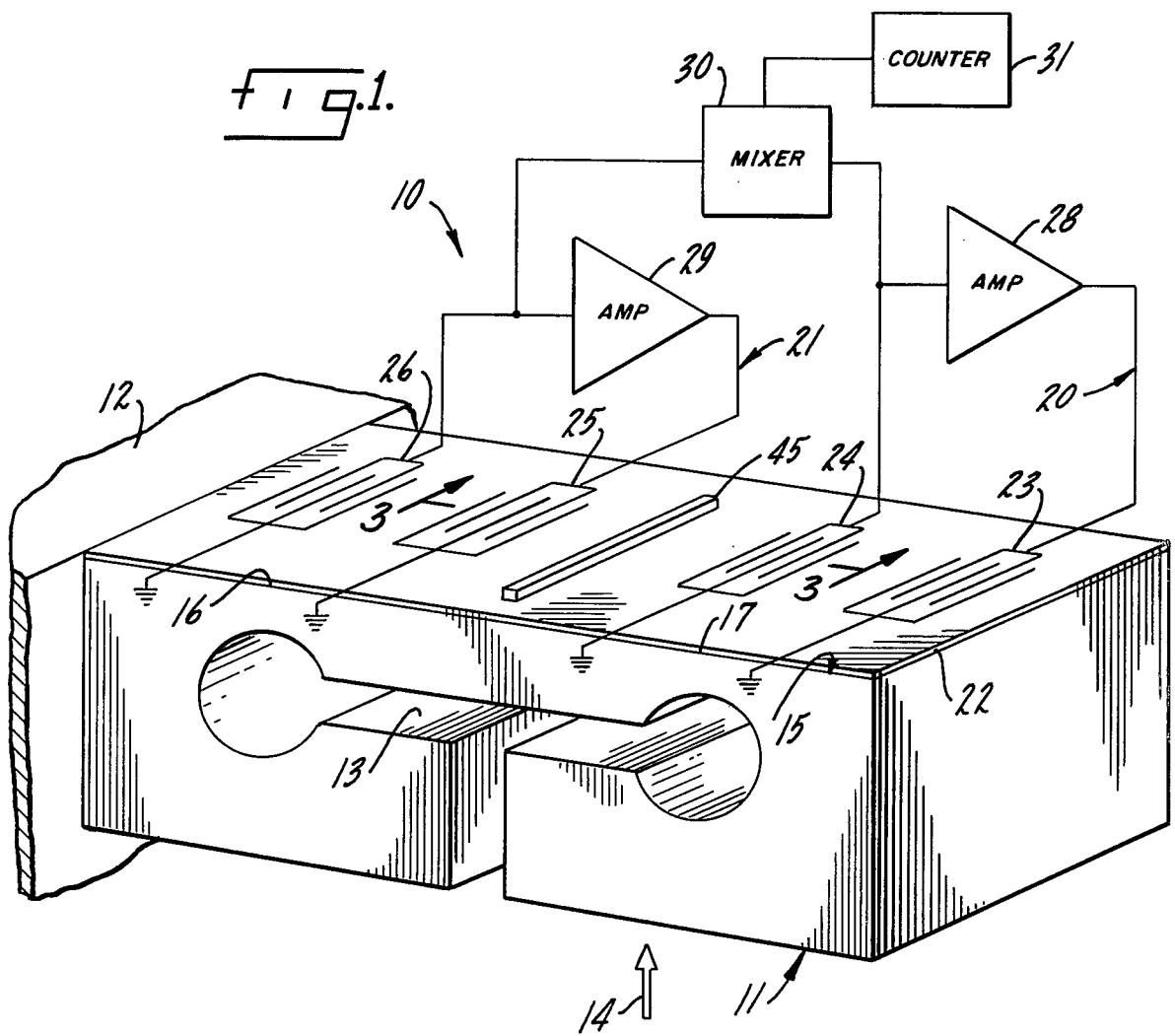
FIG. 1 is a greatly enlarged perspective, partically schematic, of a sensor embodying the present invention.
Figure 4A:
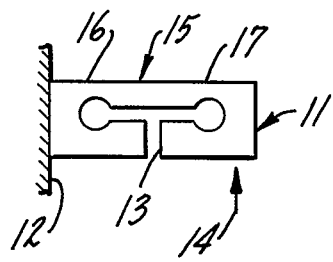
FIGS. 4a and 4b are partially diagrammatic side elevations of the sensor shown in FIG. 1 indicating, through exaggeration, the type of surface deflection obtained.
Figure 4B:
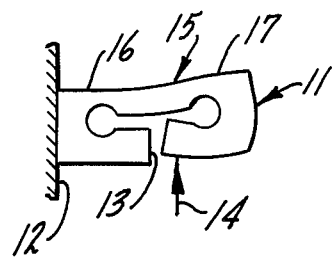

Turning now to FIG. 1, there is shown a sensor 10 including a resilient beam 11 mounted at one end to a supporting surface 12 so that the beam extends from the surface cantilever fashion. The beam is formed with a patterned cut out central section 13 giving the beam a cross section such that a force 14 applied to the unsupported end of the beam produces a bending moment causing the beam surface 15, the upper surface in the drawing, to undulate with one portion 16 being in compression and a second portion 17 being in tension. A beam configuration such as this for a somewhat related purpose is disclosed and claimed in U.S. Pat. No. 3,341,796. The deflection effect on the beam 11 from the force 14 is shown, exaggerated, in FIGS. 4a and 4b in which the bending moment oppositely bows the surface portions 16 and 17. This is the result of stress concentrations caused by the cross sectional shape of the beam as explained in the patent referred to above.

The sensor 10 develops its output signal by comparing the frequencies of two oscillator circuits 20 and 21 in which feedback is through surface acoustic waves, i.e. Rawleigh waves, generated in the surface of a layer 22 that is adhered to and stressed along with the beam surface 15. The surface acoustic waves, or SAWS, couple pairs of transducers 23 and 24, and 25 and 26, formed of interdigitated electrodes or conductors spaced so that the surface portion 17 lies between the transmitter transducer 23 and the receiver transducer 24 of one pair, and the surface portion 16 lies between the transmitter transducer 25 and the receiver transducer 26 of the other pair. As will be familiar to those skilled in this art, an alternating electrical signal impressed on the transducers 23, 25 will generate surface acoustic waves in the adjacent piezoelectric layer surface that will travel to the receiver transducers 24, 26 and produce electrical signals at those electrodes. The oscillator circuits 20, 21 are completed by grounding one set of conductors in each of the transducers 23–26 and coupling the other set of conductors in the transmitter and receiver transducers by amplifiers 28 and 29. The amplifiers establish a loop gain greater than one, the loop being completed by way of the SAW to cause resonance at frequencies dependent on the rate of SAW propagation, an distances, between the transmitter and receiver transducers.

In carrying out the invention, the frequencies of the circuits 20, 21 are compared by a circuit 30 and the frequency difference, if any, is applied to a counter 31 which serves as the digital readout device of the sensor 10. The circuit 10 may take the form of a mixer capable of detecting the difference frequency between the frequencies of the oscillators. When no force is applied to the beam, this difference frequency will be zero. Furthermore, because the SAW's travel in what is essentially the same surface, variations in wave propagation rate attributable to temperature changes affect both circuits 20 and 21 equally so that no frequency difference signal would be sent to the counter 31. However, upon deflection of the beam 11, compression in the surface portion 16 and tension in the portion 17 speeds and slows, respectively the SAW propagation rate, as well as oppositely varying the distances between the transducer pairs, thereby changing the resonating frequencies of the oscillating circuits 20, 21. The resulting frequency difference, detected in the circuit 30 and read out in digital form by the counter 31, is directly proportional to the deflection of the beam 11, which in turn is directly proportional to the force 14 causing that deflection — at least within the elastic limits of the beam material.

In FIG. 2, a simplified and somewhat more compact sensor 10a is shown in which parts corresponding to those described above have been given the same reference number with the distinguishing suffix a added. Thus, the sensor 10a includes a beam 11a fixed to a surface 12a and with a cut out section 13a causing a force 14a to put surface portion 16a in compression and surface portion 17a in tension. A pair of oscillating circuits 20a and 21a, including SAWs in the surface of a layer 22a and amplifiers 28a and 29a, have their frequencies compared by a circuit 30a and read out by a counter 31a.

In this embodiment, only three transducers 35, 36 and 37 are used to form the circuits 20a, 21a with the transducer 36 serving as a common transmitter for each of the receiver transducers 35, 37 spaced on opposite sides of the transducer 36. The SAW wave paths in the circuits include the portion 16a between the transducers 35, 36 and the surface portion 17a between the transducers 36, 37.

In the FIGS. 1 and 3a embodiment, the layer 22 is piezoelectric crystal such as Zno or CdS adhered directly to the surface 15 of the beam 11, and the conductive portions of the transducers are formed directly on the outer, SAW carrying surface 41 of the layer 22. Alternatively, in the embodiment shown in FIG. 3b in which parts previously described have been given the same reference numbers with distinguishing suffix b added, the layer 22b is a dielectric such as $SiO_2$ or $Al_2O_3$ adhered directly to the surface 15b of the beam 11b. The transducers in this case include conductors formed on the layer 22b with piezoelectric portions 42 and 43 formed over the conductors and on to the layer 22b. The SAWs are generated in the transducers and are propagated in the surface 41b.

In accordance with the invention, the resilient beam 11, 11a or 11b is formed of highly elastic but rugged material such as steel, and the layers 22 or 22b, the conductors of the transducers 23–26 or 35–37, and the piezoelectric material either as the layer 22 or as portions 42 and 43, are all formed on the beam using microelectronic film techniques. In this way, the fragility of an all crystal or an all ceramic deflection element is avoided, and a structure is achieved that can be economically produced in volume. Depositing the various structures as layers on the beam intimately couples those layers with the undulating beam surface so that the piezoelectric material is stressed along with that beam surface.

As those familiar with this art will appreciate, the layers 22 and 22b should be two or three times thicker than the wave length of the generated SAWs, which wave length is determined by the spacing of the interdigitated conductors in the transducers.

To prevent or at least minimize cross talk between the oscillator transducers, acoustic wave absorbers 45, 45a and 45b are deposited to attenuate surface wave energy and thus acoustically shield the transducers.

Those familiar with this art will also appreciate that the sensors 10 and 10a are quite economical to manufacture but will, nevertheless, give accurate digital information reflecting the amount of force transmitted to the beam 11 or 11a, with the sensor being fully temperature compensating. It can also be seen that the sensor is rugged and quite resistant to shock and mechanical vibration.

Since the force on the beam 11 or 11a is reflected by changes of electrical signal frequency, and since frequency counters have become relatively commonplace items of electronic hardware, the sensor is well suited for economically providing digital read out of the forces being sensed.

I claim as my invention:

1. A sensor comprising, in combination, an elastic beam formed of metal anchored at one end and having a cross section such that a bending force near the other end causes a planar surface of the beam to undulate with a first portion of said surface being in tension and a second portion of said surface being in compression, transducers adhered to said beam surface and comprising interdigitated conductors formed at the surface of a piezoelectric layer, a pair of amplifiers respectively coupling said transducers to form a pair of oscillator circuits including surface acoustic waves in a pair of wave paths between the transducers with the acoustic wave paths including, respectively, said first and second beam surface portions, and means for comparing the oscillating frequencies of said circuits and generating an output signal based on the frequency variation that will reflect the value of said bending force.

2. The combination of claim 1 in which the piezoelectric layer of said transducers and said conductors are deposited on said beam as films.

3. The combination of claim 1 in which there are two pairs of said transducers with one pair spaced to define one of said wave paths and the other pair spaced to define the other one of said wave paths.

4. The combination of claim 1 in which there are three of said transducers including a centered transducer and two other transducers spaced on opposite sides of the centered transducer to define said pair of wave paths.

5. The combination of claim 1 in which said piezoelectric layer is adhered directly to said beam surface and said conductors are formed on the outer surface of said piezoelectric layer, said wave paths being in said outer surface.

6. Th combination of claim 1 including a dielectric layer adhered to said beam surface, said transducer conductors being formed on the outer surface of said dielectric layer, and the piezoelectric layer of said transducers being formed over said conductors on said outer surface, said wave paths being in said outer surface.

7. A sensor comprising, in combination, a beam anchored at one end and having a cross section such that a force applied to the beam causes a planar surface, consisting of a single sheet, of the beam to undulate with a first portion of said surface being in tension and a second portion of said surface being in compression, said beam being formed of highly elastic metal and having a layer of piezoelectric material conforming with said surface, a first SAW oscillator circuit comprising a first pair of transducers and amplifier coupling said transducers, a second SAW oscillator circuit comprising a second pair of transducers and amplifier coupling said transducers, said transducers comprising interdigitated conductors on said piezoelectric layer with said first pair being associated with said first portion of said surface and said second pair being associated with said second portion of said surface so that application of a force to said beam causes the frequencies of the respective oscillator circuits to vary in opposed directions, and means for comparing the oscillating frequencies of said circuits and generating an output signal based on the frequency variation that will reflect the value of said bending force.

* * * * *